United States Patent
Clendennen et al.

(10) Patent No.: US 7,179,960 B2
(45) Date of Patent: Feb. 20, 2007

(54) SEED-ASSOCIATED PROMOTER SEQUENCES

(75) Inventors: Stephanie K. Clendennen, Kingsport, TN (US); Jonathan Lightner, Mulino, OR (US); Debra K. Schuster, Portland, OR (US)

(73) Assignee: Exelixis Plant Sciences, Inc., South San Francisco, CA (US)

( * ) Notice: Subject to any disclaimer, the term of this patent is extended or adjusted under 35 U.S.C. 154(b) by 349 days.

(21) Appl. No.: 10/633,279

(22) Filed: Aug. 1, 2003

(65) Prior Publication Data

US 2004/0064854 A1 Apr. 1, 2004

Related U.S. Application Data

(60) Provisional application No. 60/400,170, filed on Aug. 1, 2002.

(51) Int. Cl.
*C12N 15/82* (2006.01)
*A01H 5/00* (2006.01)
*A01H 5/10* (2006.01)

(52) U.S. Cl. ............... 800/287; 800/298; 536/24.1; 435/320.1; 435/419; 435/468; 435/430

(58) Field of Classification Search .......... 536/24.1; 435/419; 800/298
See application file for complete search history.

(56) References Cited

FOREIGN PATENT DOCUMENTS

EP 0571741 A2 1/1993

OTHER PUBLICATIONS

Kim Y et al. A 20 nucleotide upstream element is essential for the nopaline synthase (nos) promoter activity. Plant Mol Biol. Jan. 1994;24(1):105-17.*
de Pater S et al. A 22-bp fragment of the pea lectin promoter containing essential TGAC-like motifs confers seed-specific gene expression. Plant Cell. Aug. 1993;5(8):877-86.*
Fiedler U. et al. A complex ensemble of cis-regulatory elements controls the expression of a Vicia faba non-storage seed protein gene. Plant Mol Biol. Jul. 1993;22(4):669-79.*
Garcia-Mas,J., et al., "Molecular characterization of cDNAs corresponding to genes expressed during almond (*Prunus amygdalus* Batsch) seed development.", Plant Mol Biol., Jan. 1995, 205-10, 27-1.
Schubert,R., et al., "Tissue-specific expression of an oat 12S seed globulin gene in developing tobacco seeds: differential mRNA and protein accumulation.", Plant Mol. Biol., Jun. 1994, 203-10, 26.
Garcia-Mas,J., et al., "*P. amygdalus*, Batsch (Texas) pru1 mRNA.", Genbank GI No. 460805 [online], Jul. 7, 1995 [retrieved Jan. 14, 2005]. Retrieved from the Internet:<URL:http://www.ncbi.nlm.nih.gov/entrez/query.fcgi?CMD=Display&DB=nucleotide>.
EMBL-EBI Database, Accession No. X78119, *P. amygdalus*, Batsch (Texas), pru1 mRNA, Mar. 14, 1994 (Rel. 38, Created).
Lycett et al., "The 5'-flanking regions of three pea legumin genes: comparison of the DNA sequences," *Nucl. Acids Res.*, 13(18):6733-6743, 1985.
Rerie et al., "Developmental and environmental regulation of pea legumin genes in transgenic tobacco," *Mol. Gen. Genet.*, 225:148-157, 1991.
Hu and Poulton, "Sequencing, Genomic Organization, and Preliminary Promoter Analysis of a Black Cherry (R)—(+)-Mandelonitrile Lyase Gene," *Plant Physiol.*, 115:1359-1369, 1997.
Goossens et al., "The arcelin-5 Gene of *Phaseolus vulgaris* Directs High Seed-Specific Expression in Transgenic *Phaseolus acutifolius* and Arabidopsis Plants," *Plant Physiol.*, 120:1095-1104, 1999.
Keddie et al., A seed-specific *Brassica napus* oleosin promoter interacts with a G-box-specific protein and may be bi-directional, *Plant Mol. Biol.*, 24:327-340, 1994.
Xie et al., "Bidirectionalization of polar promoters in plants," *Nature Biotechnology*, 19:677-679, 2001.
Sadanadom et al., "Identification of a peptide methionine sulphoxide reductase gene in an *oleosin* promoter from *Brassica napus*," *Plant J.*, 10(2):235-242, 1996.

* cited by examiner

*Primary Examiner*—Cynthia Collins
(74) *Attorney, Agent, or Firm*—Klarquist Sparkman, LLP (57) ABSTRACT

Plant promoters that exhibit seed-associated expression are described, including bi-directional promoters capable of directing seed-associated expression in either orientation.

26 Claims, 2 Drawing Sheets

```
CACAAGGAAT GAGAAGGAGA TAGATGACTT GTGATTCGAG CTCACTTGTA TCTTGTGTTT
---------- ----ACATAT TTGGAGACTA CAGAAAGGAG AGAGAAAGCT CTTTGGTTTT
           *          * *  ****   **  ***        *       ***  ***
                                                            (1)
GAGATGG-TG AAGCAACGAG CGGTGGGCGC TGGTATTTGT AGGAGGGAAA ATGAGTTGAG
GAGATGGGTG AAGCGGCGAG CAGCAGGCGC TGGTATTTAT AGTGAAGAAG AGGAGGTGAG
******* ** ****  **** * * ***** ********* * **    ***   *  *** ****

(2)
GCGTGGACAC GTAGAGTTTC GTGTGTAAGG CATCTTTTGC CATTCTTCTA CTTGCATGGC
GGAGAGACAC GTAGGGAAAT GAGTGTAAGG AATCCTTCGC CATTATTCTG *CTTGCATG*GC
 *   ***** ****  *     * ******** *** ** ** **** ****  *********

TTTGAGGCTT TGAATTGTTA ACACCTCATT TTGTGTAGCA GGGGCAGCAG GCTATATGCG
TTTGAAGCTC TGAATTGTTT ACACCTCATT TTGTGGTTTA GGG----CAG GTGGCTTTCG
*****  *** ********* ********** *****   *   ***    ***  *   * **

GCAACCAGCG GTGGGGTTCC TCGTCAATAT TGTTGTCTGG TTCTGAGCTT GATTTGCACC
GCT-TCAGAG AAAAAA--CA AAGTGAGTTG AGTTATGTGG CAACCAGGTG GG--TGTCTC
**   *** *               *       ** * *   ***  *  **   **    *

TGGCCGTT-T GGTGAAGTAA AATTCATGGG ACTTGGGATC CGAACCCGGG CCCATATGAC
GAGCCATTGT TGTTTTCTTA CTGTCTTGGG ATT---GGTG CGTTTCTGAA ACCCTTTTGG
  *** ** *  **        * * ****  **    * *   *  * **   ***  **  *

(3)
TGTGCGTGCT TGGTGAGAAA CGTGAACTCC ACCTGATTGT CTGTGATGAG TTTAATTGGT
CAT---TGCC TGC***TGAGAAA CGTGAACTCC ATCTGATCGT*** CTCTGATCAG TTTTGGTGGG
 *     *** **  ****** ********** *  ***** ** ** **** ** ***    ***

TTTTTTTGTT TAAATGTTTG GTCAAATTTG TTTTACTCGG AACAAATTGT TAAGCCTCTG
TTCCATTGTT TTGTTGCCAA TCCTCATTCA TATT-CTCTC TCCTTTTATG TAAAAGTAAA
**   ***** *  **        *  ***  * ** ***     *   *    ***   *

CTCTATAAGA AATAAAAAAC GTTGTTTTGT GAACTAAAAC GCAATCTTTT GGCTTAGTTG
---TATTTGA GTTATTATAA TTTGGGTACC ACTCTAATAT TCTCTCTCCT TTTTTTCTTT
   ***  **  ** *  *  ***   *    ****  *   * ***   *    ** **

AGCCAAGAGG GTTCT---CT CTCTACAGTT CCAAATC-CA AAACCCACAA CTTCAATGAA
TAAAGAAAAG CTTCCAAGTT TTTTATAGGA TCAATTTGTA AAGTATGAAA TGCTTTTGTT
 * *   ***    *    *   * ** **    *** *  *   *    **     **

ATTACGAATG AATGACCTCC ACTACCACTA GTATGAATTC TTTTGTATTT TCCTGTCAAG
GTTCTAAGTA GCTGATCTCT --TGTTGGCC TTTTTGCTTG ACAGGAAAAT ACAAAAGAAT
 **   *    *** ***     *           *   **  *     *   *   *   **

CAAAAAGGCC AACAA--GAG ATCAGCTACT TAGAACAACA AAAGCATTTC ATACTTTACA
TCATACTAGT GGTAGTGGAG GTCATTCATT CGTAATTTCA TTGAAGTTGT GGGTTTTG-G
 *  *       *  ***   *** ***   *    **  ** ** **    **    ***
```

FIG._1A

```
AATTGATCCT ATAAAAAACT TGGAAGCTTT TCTTTAAAAG AAAAAAAGGA GAGAGAATAT
ATTTGGAACT GTAGAGAG-- -AGAACCCTC TTGGCTCAAC TAAGCCAAAA GATTGCGTTT
* ***     **       ** * *         *** *  *     **    **   *  ** *  * *

TAGAGTGGTA CCCAAATTAT AATAACTCAA ATA---TTTA CTTTTACATA AAAGGAGAGA
TAGTTCACAA AACAACGTTT TTTATTTCTT ATAGAGCAGA GGCTTAACAA TTTGTTCCGA
***     *  ***    * * **    **  ***      * ***    *   *       **

G-AATATGAA TGAGGATTGG CAACAAAACA ATGGAACCCA CCAAAACTGA TCAGAGACGA
GTAAAACAAA TTTGACCAAA CATTTAAACA AAAAAAACCA ATTAAACTCA TCACAGACAA
* **  **   * *        **   ***** *   ** *** ***** * *** **** *

(3)
TCAGATGGAG TTCACGTTTC TCAGCAGGCA ---ATGCCAA AAGGGTTTCA GAAACGCACC
TCAGGTGGAG TTCACGTTTC TCACCAAGCA CGCACAGTCA TATGGGCCCG GGTTCGGATC
**** ***** ********** *** ** ***    *    *  * **    *   ** * *

---AATCCCA AGACAGTAAG AAAACAACAA TGGCTCGAGA CA--CCCACC TGGTTGCCAC
CCAAGTCCCA TGAATTTTAC TTCACCA-AA CGGCCAGGTG CAAATCAAGC TCAGAACCAG
   * *****  **    *  *   ** * ** ***   *    **   * * *       ***

ATAACTCAAC TCACTTTG-- TTTTTTCTCT GAA-GCCGAA AGCCACCTGC ----CCTAAA
ACAACAATAT TGACGAGGAA CCCCACCGCT GGTTGCCGCA TATAGCCTGC TGCCCCTGCT
* ***     * * **    *    * ** *   **** *    *****      ***

(2)
CCACAAAATG AGGTGTAAAC AATTCAGAGC TTCAAAGCCA TGCAAGCAGA ATAATGGCGA
ACACAAAATG AGGTGTTAAC AATTCAAAGC CTCAAAGCCA TGCAAGTAGA AGAATGGCAA
 ********* ****** *** ****** *** ********* ****** *** * ****** *

(1)
AGGATTCCTT ACACTCATTT CCCTACGTGT CTCTCCCTCA CCTCCTCTTC TTCACTATAA
AAGATGCCTT ACACACGAAA CTCTACGTGT CCACGCCTCA ACTCATTTTC CCTCCTACAA
* *** **** ****  *    * ******** *  *****  *** * ***     *** **

ATACCAGCGC CTGCTGCTCG CCGCTTCACC CATCTCAAAA CCAAAGAGCT TTCTCTCTCC
ATACCAGCGC CCACCGCTCG TTGCTTCACC -ATCTCAAAC ACAAGATACA AGTGAGCTCG
********** *  * ***** ********* ********* ***    *       ***

TTTCTGTAGT CTCCAAATAT GT---------------
AATCACAAGT CATCTATCTC CTTCTCATTCCTTGTG
**    ***  *   * * *  *
```

FIG._1B

SEED-ASSOCIATED PROMOTER SEQUENCES

RELATED APPLICATIONS

Priority is claimed to U.S. provisional application No. 60/400,170, filed Aug. 1, 2002, the contents of which are incorporated by reference.

BACKGROUND OF THE INVENTION

The field of the invention is plant seed-associated promoters.

There is substantial interest in identification and isolation of regulatory elements that control gene expression in plant seed; such seed-specific and seed-associated promoters may be used in the generation of transgenic plants with desired seed traits. For instance, seed specific regulatory elements are useful for manipulating lipid metabolism, especially fatty acid synthesis in seed, and for enhancing agronomic traits such as herbicide and pesticide resistance and drought tolerance.

Seed storage proteins genes are among the most tightly regulated plant genes. Seed storage protein expression is highly seed-specific, and the corresponding transcripts accumulate to high levels in the middle to late stages of seed development. Many seed storage protein genes have been cloned from diverse plant species, and their promoters have been analyzed in detail (see, e.g., Thomas, 1993, Plant Cell 5:1401–1410). Promoter elements, which constitute the 5'-upstream regulatory regions, have been functionally defined by their ability to confer seed-specific expression of the bacterial beta-glucuronidase (GUS) reporter gene in transgenic plants (e.g., Bogue et al. 1990, Mol Gen Genet 222:49–57; Bustos et al. 1989, Plant Cell 1:839–853). Deletion analysis of these promoters has allowed researchers to define regions within each promoter that are critical to its overall regulation (Bustos et al. 1991, EMBO J. 10:1469–1479; Chung, 1995, Ph.D. Dissertation, Texas A&M University; Nunberg et al 1994, Plant Cell 6:473–486).

In some cases, cis-regulatory elements have been mapped and the trans-acting factors that confer functionality have been cloned. The cis-acting elements that regulate seed storage protein expression have been found in genes from a variety of plant species including rice, sunflower, French bean and soybean. Conserved nucleotide sequences that are commonly found in seed-specific regulatory regions have been identified and include the legumin-box (leg-box), which comprises a core element of CATGCATG, also called an RY repeat element.

The napin promoter (from the napA gene encoding the *Brassica napus*, 2S storage protein) is widely used to control expression of lipid biosynthetic genes in transgenic plants (Josefsson et al., 1987, J Biol Chem 262:12196–201; Stalberg et al., 1993, Plant Mol Biol 23:671–83; Ellerstrom et al., 1996, Plant Mol Biol 32:1019–27). The *Brassica napus* oleosin promoter directs reporter gene expression in the embryo and endosperm (Keddie et al., 1994, Plant Mol Biol 24:327–40). In Arabidopsis, the FAE1 promoter has been used to control expression of the GUS reporter in developing embryos, where activity was detected as early as 4–5 days after fertilization (Rossak et al., 2001, Plant Mol Biol 46:717–25). The legumin promoter (LeB4; Baumlein et al., 1991, Mol Gen Genet 225:121–8; Baumlein et al., 1992, Plant J 2:233–9) from the legume Vicia faba has also been functionally characterized and shown to promote seed-specific expression of heterologous genes. The characterization of seed-specific promoters was reviewed in Goossens et al., 1999 (Plant Pyhsiol 120:1095–1104).

The vast majority of native plant promoters are unidirectional, with one upstream (5') promoter directing only one gene that is 3' to the promoter. Bidirectional promoters exist in some prokaryotes and viruses, and bi-directional promoters that are active in plants have been identified from viral (geminivirus; Frey et al., 2001, Virus Genes 22:231–42) and bacterial (*Agrobacterium*; Schmulling et al., 1989, Plant Cell 1:665–70; Leung et al., 1991, Mol Gen Genet 230:463–74) plant pathogens. A strategy for engineering bidirectional promoters, essentially by adding a minimal promoter region to the upstream end of a uni-directional promoter, has been proposed (Xie et al., 2001, Nat Biotechnol 19:677–9). Additionally, a bidirectional promoter from *Brassica napus* has been characterized wherein the regulatory region controls seed-specific expression in one direction while in the opposite orientation, the promoter directs expression in a variety of tissues including leaves and roots (Keddie et al., 1994, Plant Mol Biol 1994 24:327–40; Sadanandom et al., 1996, Plant J 10:235–42). However, no plant promoters that control seed-associated expression in both orientations have been described.

Globulins and albumins are common seed storage proteins in dicotyledonous plants (dicots). These proteins can be distinguished from each other based on differential solubility; albumins are water soluble, whereas globulins are soluble in salt solutions. In many dicots, including citrus and almond (*Prunus amygdalus*), 12S globulins are the most prevalent seed storage proteins. 12S globulins are multimeric proteins composed of dimer subunits. Each dimer contains a 30–40 kDa alpha-subunit and a 20 kDa beta-subunit. The dimer subunits are derived from a single precursor polypeptide that undergoes several post-translational modifications, including cleavage of a signal peptide followed by cleavage of the pre-protein into the alpha and beta subunits.

Two full-length cDNA clones encoding the prunin 12S globulin seed storage proteins (Pru1 and Pru2) have been isolated from almond (*Prunus amygdalus* cv Texas; Garcia-Mas et al., 1995, Plant Mol Biol 27:205–10). Each transcript encodes a pre-protein that is processed to create the alpha and beta subunits that comprise the ~60 kDa mature seed storage protein. At the amino acid level, Pru1 and Pru2 are 63% identical, with Pru2 containing two gaps in the region corresponding to the alpha subunit. The two prunin transcripts are seed-specific and are among the most abundant in immature seeds. It appears that the main storage proteins in almond are legumin-like globulins that consist of two main pairs of polypeptides, each pair encoded by a single gene (Garcia-Mas et al., 1995).

SUMMARY OF THE INVENTION

The invention is directed to a PRU promoter having seed-associated promoter activity that comprises in 3' to 5' direction, the following regions: (a) a core promoter sequence containing a TATA-box, and (b) a sequence conferring seed specificity that contains a motif with similarity to the legumnin-box consensus CATGCATG. In some embodiments the PRU promoter additionally comprises (c) an upstream sequence motif which is predicted to function as an enhancer element. In some embodiments, the PRU promoter is bi-directional, having a complementary strand that also comprises regions (a) and (b), and optionally (c). In one aspect of the invention, the bi-directional PRU promoter is used in a double-stranded plant expression vector that comprises, in the 5' to 3' orientation, a first heterologous protein encoding sequence in the antisense direction, the PRU promoter, and a second heterologous encoding sequence in the sense direction, wherein the PRU promoter directs seed-associated expression of both the first and the second heterologous protein encoding sequences.

DESCRIPTION OF THE FIGURE

FIGS. 1A and 1B show an alignment of the complete nucleotide sequence of the ChPRU promoter (top strand in FIG. 1; SEQ ID NO:1) with its reverse complement (bottom strand; SEQ ID NO:6). The following features are indicated in bold, italicized text for each sequence: (1) the putative TATA-box, (2) motif with similarity to the leguinin-box consensus CATGCATG, and (3) an upstream sequence motif common to both orientations of the chPRU promoter. Each of these features is associated with regions of high identity between the ChPRU promoter sequence and its reverse complement, indicated by underlining, and are predicted to function as (1) core promoter sequences, (2) sequences conferring seed-specificity, and (3) enhancer elements.

DETAILED DESCRIPTION OF THE INVENTION

The present invention provides isolated nucleic acid sequences corresponding to promoters that direct seed-specific expression in a plant seed. The present invention provides chimeric genes, DNA constructs, and plant transformation vectors that are useful for the expression of heterologous genes and for the generation of transgenic plants tissue having desired traits.

PRU Promoter Sequences

We identified putative cherry (*Prunus avium*) orthologs of the almond (*Prunus amygdalus*) prunin gene, and recovered the associated promoter sequence, which we have designated the "chPRU promoter". As used herein, the term "promoter sequence" refers to a sequence of a DNA molecule that directs transcription of a downstream gene to which it is operably linked. The term "operably linked" relative to a recombinant DNA construct or vector means that nucleotide components of the recombinant DNA construct or vector are in a functional relationship with another nucleic acid sequence. More specifically, in the context of a promoter, "operably linked" means that the transcription or translation of the heterologous nucleotide sequence is under the influence of the promoter sequence. For example, a promoter is operably linked to a coding sequence if it affects the transcription of the sequence. Sequences that are operably linked are often but not always contiguous (for example, enhancers are often not contiguous with the sequences whose expression they affect).

The isolated promoter was found to direct high-level seed-associated gene expression when operably linked to heterologous coding sequences. As used herein, the terms "isolated PRU promoter" and "chPRU promoter" refer to a nucleic acid comprising the sequence provided in SEQ ID NO:1 or the reverse complement thereof, SEQ ID NO:6. The term also encompasses fragments and derivatives thereof that retain seed-associated promoter activity as discussed in more detail below. As used herein, the term "seed-associated promoter" refers to a promoter that directs RNA synthesis at higher levels in seeds than in other cells and tissues. A "seed-specific" promoter is a seed-associated promoter that directs RNA synthesis essentially only in the seed. But, under certain conditions and using particular detection methods, very low levels of expression in tissue other than seed may be detected from a seed-specific promoter.

We have found that the chPRU promoter is bi-directional in that it directs expression of genes that flank it on either side, which we have designated ChPru1 and ChPru2. The sequence provided in SEQ ID NO:1 is in the same 5' to 3' orientation as the sense orientation of the gene that has the higher homology to almond Pru2, which we have designated chPru2. Its reverse complement (SEQ ID NO:6) is in the same 5' to 3' orientation as the gene that we have designated chPru1. It will be understood by one of skill in the art that a double-stranded nucleic acid molecule (e.g., DNA) comprising a specific sequence inherently comprises the reverse complement of that sequence. However, since sequences in one or the other orientation may be important for particular utilities, since there may be occasions in which single-stranded nucleic acid molecules are used, and since the isolated PRU promoter functions in a bi-directional manner, the sequences in both orientations are specifically recited.

In a preferred embodiment, the PRU promoter of the present invention is bi-directional, and comprises the sequence provided in SEQ ID NO:1. In another preferred embodiment, the PRU promoter of the present invention comprises the reverse complement of the sequence provided in SEQ ID NO:1, as provided in SEQ ID NO:6. The PRU promoter sequences may also be defined as the sequences that are naturally located upstream from the translational start codon of a chPru1 or chPru2 gene in the cherry genome, which sequences are capable of directing seed-associated expression of chPru1 or chPru2. The chPru1 and chPru2 genes may be identified by fragments of their coding sequences, which are disclosed herein as SEQ ID NO:2 (chPru1) and SEQ ID NO:3 (chPru2). The predicted start codon of chPru1 is at nucleotides 1–3 of SEQ ID NO:2. There are two potential start codons predicted for chPru2, and these are located at nucleotides 1–3 of SEQ ID NO:3 and at nucleotides 7–9 of SEQ ID NO:3 (the reading frame of the protein would not be affected by which start codon was used).

While the entire sequence of an isolated PRU promoter is sufficient for seed-associated promoter activity, smaller or altered sequences will also be sufficient. Thus, included within the scope of PRU promoters of the present invention are derivatives (including fragments and variants) of the isolated PRU promoters, which derivatives are capable of directing seed-associated expression of heterologous genes to which the promoters are operably linked; such derivatives are termed "functionally active."

In one embodiment, derivatives include insertions, deletions (including 5' and/or 3' truncations) and substitutions of one or more nucleotides. Such derivatives may be naturally occurring (e.g., polymorphic sequences) or may be synthetic (including variants of the disclosed sequences that result from site-directed or random mutagenesis) and may be obtained using methods known to those skilled in the art. Methods by which one may empirically determine whether a candidate derivative sequence is sufficiently homologous to the isolated PRU promoter to—direct seed-associated gene expression are well known in the art and are described herein.

It is expected that fragments of the disclosed chPRU promoter sequences that retain seed-associated promoter activity will minimally comprise a core promoter domain and a domain that confers seed-specifidty. These regions are contained within nucleotides 1055–1212 of SEQ ID NO:1, and nucleotides 1043–1198 of SEQ ID NO:6. Thus, in one embodiment of the invention, the derivative chPRU promoter is uni-directional and comprises a nucleotide sequence selected from nucleotides 1055–1212 of SEQ ID NO:1, and nucleotides 1043–1198 of SEQ ID NO:6. Preferably, the derivative chPRU promoter additionally comprises a putative enhancer domain, and thus comprises a nucleotide sequence selected from nucleotides 854–1212 of SEQ ID NO:1, and nucleotides 827–1198 of SEQ ID NO:6.

Figure 1A:
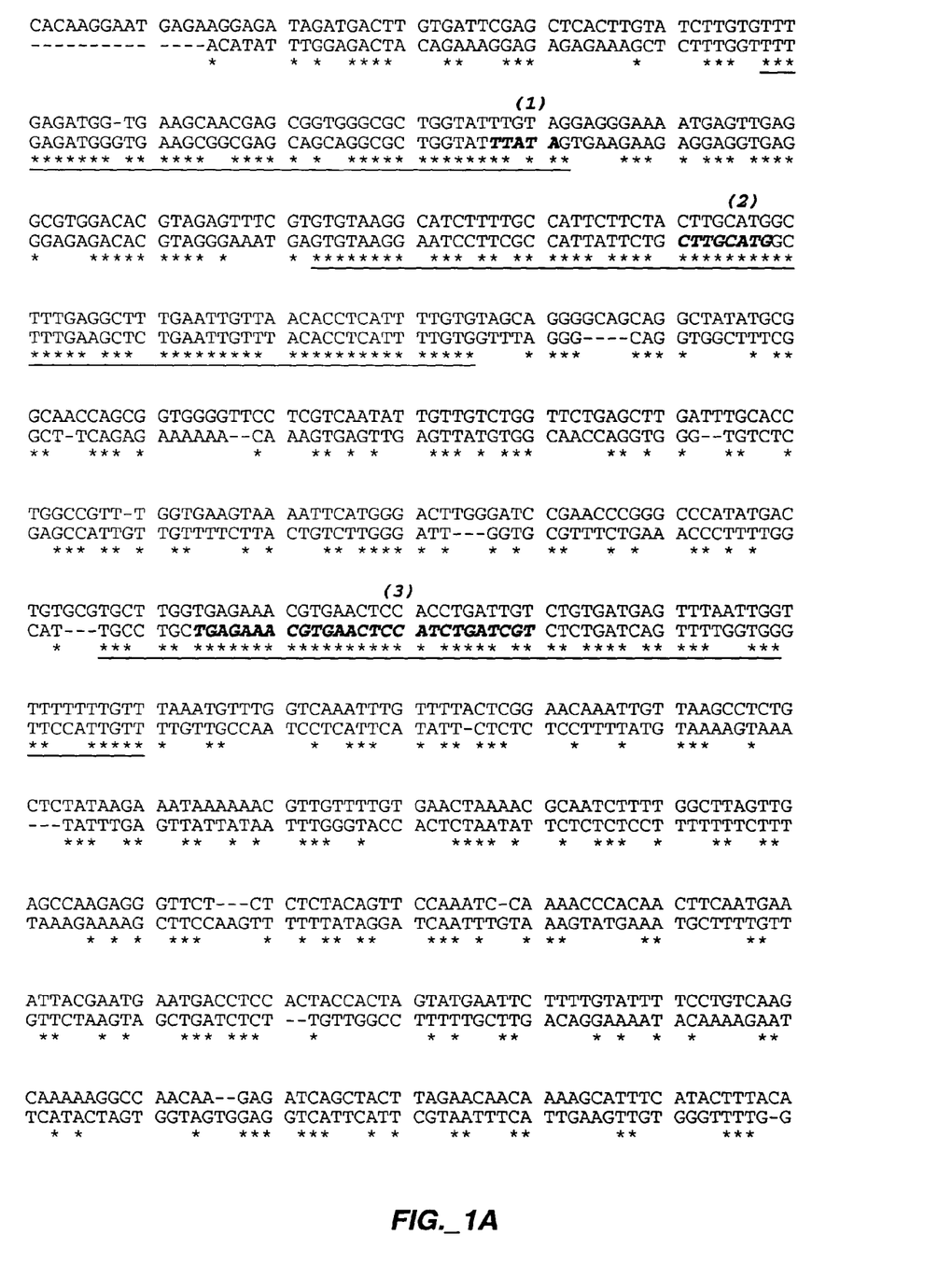

FIG. 1 can be referenced for guidance in making derivative chPRU sequence that share less than 100% identity with SEQ ID NOs:1 and 6, and fragments thereof. In general, regions that share high identity wit an alignment of SEQ ID NO:1 (top strand) and its reverse complement (bottom strand; SEQ ID NO:6) are expected to contribute to the seed-associated promoter function and should generally be conserved in derivative chPRU promoter sequences. These regions are underlined in FIG. 1. Regions of lower identity are expected to be unnecessary for the seed-associated promoter function, and thus can vary substantially in corresponding derivative sequences, e.g. they can vary in length (i.e. can serve as spacer regions of varying length) and/or can vary in sequence identity. The sequences within SEQ ID NO:1 that are predicted to function as (1) core promoter sequence, (2) sequence conferring seed-specificity, and (3) enhancer element, as shown in FIG. 1, are set forth in SEQ ID NOs: 7–9, respectively. And, the sequences within SEQ ID NO:6 that are predicted to function as (1) core promoter sequence, (2) sequence conferring seed-specificity, and (3) enhancer element, are set forth in SEQ ID NOs:10–12, respectively.

SEQ ID NOs 7 and 10, which correspond to the predicted core promoter regions of the chPRU promoter, share approximately 85% sequence identity with each other. Thus, a derivative chPRU sequence preferably comprises a core promoter region that shares at least 80% sequence identity with SEQ ID NO:7 or 10, and preferably at least 85% sequence identity with SEQ ID NO:7 or 10. As used herein, "percent (%) sequence identity" with respect to a specified subject sequence, or a specified portion thereof, is defined as the percentage of nucleotides in the candidate derivative sequence identical with the nucleotides in the subject sequence (or specified portion thereof), after aligning the sequences and introducing gaps, if necessary to achieve the maximum percent sequence identity, as generated by the program WU-BLAST-2.0al9 (Altschul et al., J. Mol. Biol. (1997) 215:403–410; http://blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides divided by the sequence length for which the percent identity is being reported.

SEQ ID NOs 8 and 11, which correspond to the seed-specificity conferring regions of the chPRU promoter, share approximately 87% sequence identity with each other. Thus, a derivative chPRU sequence, in addition to the above-described core promoter region, additionally comprises a sequence that confers seed-specificity that shares at least 80% sequence identity with SEQ ID NO:8 or 11, and preferably at least 85% sequence identity with SEQ ID NO:8 or 11.

As indicated above, it is expected that a core promoter region and seed-specificity conferring region are sufficient for seed-associated promoter activity. Thus, in one embodiment of the invention, a derivative chPRU promoter comprises from the 5' to 3' direction a sequence that confers seed-specificity, and a core promoter sequence. In preferred embodiments, the derivative chPRU promoter additionally comprises a putative enhancer element that is upstream (i.e. 5') of the seed-specificity conferring region. SEQ ID NOs 9 and 12, correspond to the predicted enhancer regions of the chPRU promoter, and share approximately 80% sequence identity with each other. Thus, a derivative chPRU sequence preferably comprises a putative enhancer region that shares at least 75% sequence identity with SEQ ID NO:9 or 12, and preferably at least 80% sequence identity with SEQ ID NO:7 or 10.

Derivative sequences may be identified by their ability to hybridize to an isolated PRU promoter under stringent hybridization conditions. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 or the complement or thereof under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18–20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate). In other embodiments, moderately stringent hybridization conditions are used that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1Ficol™, 1% BSA, and 500 µg/ml denatured salmon sperm DNA; hybridization for 18–20 h at 40° C. in a solution containing 35% formamide, 5×SSC, 50 mM Tris-HCl (pH 7.5), 5 mM EDTA, 0.02% PVP, 0.02% Ficoll™, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

In addition to the above-described chPRU promoters and derivatives, the present invention is directed to other promoter sequences which correspond to the same gene, i.e., an ortholog, in other plant species. We have shown that, in addition to almond and cherry, apricot (*Prunus armeniaca*), peach (*Prunus persica*), and plum (*Prunus domestica*) also express the 12S globulin as a major seed storage protein. Accordingly, a PRU promoter of the invention may be isolated from one of these species. Based on the almond Pru1 and Pru2 coding sequences (Garcia-Mas et al., 1995, supra) and the methods described herein, it would be routine for one skilled in the art to isolate PRU promoters from these species. In one example, a PCR-adapted library of genomic DNA is constructed from the species of interest (see, e.g., "PromoterFinder™ Construction Kit," CLONTECHniques, July 1996). Oligonucleotide primers are designed to the 5' sequence of almond Pru1 cDNA and are used to amplify a genomic region upstream of the homologous region from the species of interest. Exemplary oligonucleotide sequences used to amplify the cherry prunin sequence are provided in SEQ ID NOs: 4 and 5. Sequence analysis is used to confirm that the isolated promoter sequence contains a region of homology to the known prunin gene sequence.

Chimeric Genes

The invention is directed to chimeric genes (expression cassettes) comprising nucleotide sequences of the isolated PRU promoter, or a functionally active derivative thereof, operably linked to and controlling the expression of a heterologous gene. The terms "chimeric gene" and "expression cassette" refer to a protein encoding nucleotide sequence comprising sequences that are heterologous with respect to each other (i.e., not naturally occurring together). A chimeric gene of the present invention comprises a PRU promoter sequence that is heterologous with respect to the protein encoding sequences. Thus, a chimeric gene may comprise a protein encoding sequence that is native to a plant, but heterologous with respect to the operably-linked promoten Thus, the heterologous gene can be any gene other than chPRU1 or chPRU2. As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons). The term "gene" may be used interchangeably with the terms "heterologous nucleic acid coding sequence" or the term "protein encoding sequence."

An expression cassette typically includes, in the 5' to 3' direction of transcription, a transcriptional and translational initiation region comprising a subject promoter and protein encoding sequence for a heterologous gene (also referred to as a "gene of interest"). In a preferred embodiment, the expression cassette further includes, 3' to the protein encoding sequence, a transcriptional and translational termination region that is functional in plants. The termination region, which typically includes a polyadenylation site, may be native to the gene of interest or may be derived from another source (see, e.g.: Guerineau et al. 1991, Mol. Gen. Genet. 262:141–144; Sanfacon et al. 1991, Genes Dev. 5:141–149; Mogen et al. 1990, Plant Cell 2:1261–1272; Joshi et al. 1987, Nucleic Acid Res. 15:9627–9639). Convenient termination regions are available from the Ti-plasmid of *A. tumefaciens*, such as the octopine synthase and nopaline synthase termination regions. If necessary, additional regulatory elements from genes other than chPRU1 or chPRU2 sufficient to express an effective amount of the polypeptide encoded by the heterologous gene are included in the chimeric constructs.

Standard techniques for construction of such chimeric genes are well known to those of ordinary skill in the art (e.g., Sambrook et al. Molecular Cloning, 1989, Cold Spring Harbor Laboratory Press, N.Y.) and include DNA ligation, as well as chemical or enzymatic synthesis.

Gene Inhibition Constructs

The PRU promoters of the invention may be used in chimeric constructs that are designed to specifically inhibit the expression of an endogenous gene in transformed seed. Exemplary methods for practicing this aspect of the invention include, but are not limited to antisense suppression (Smith, et al., 1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al. 1990, The Plant Cell 2:270–289; van der Krol et al., 1990, Plant Mol Biol 14:457–466), or a partial cDNA sequence (Smith et al., (1990). As used herein, the term "chimeric genes and constructs of the invention" encompasses such constructs that are specifically intended to inhibit the expression of an endogenous gene Vectors The chimeric genes and constructs of the invention are typically contained within plant vectors (also referred to as "plant expression vectors" and "plant transformation vectors") that facilitate their introduction into and use in plants and plant cells. A plant expression vector contains all of the elements to express a gene in a plant (i.e., an expression cassette), and a plant transformation vector usually also contains elements that allow the expression cassette to integrate into the plant genome.

In addition to a chimetic gene or gene inhibition construct comprising a PRU promoter, vectors of the present invention may comprise other functional sequences. Exemplary sequences include selectable marker genes that permit the selection of transformed plant cells by rendering the cells resistant to an amount of an agent that would be toxic to non-transformed plant cells. Exemplary selectable marker genes include the neomycin phosphotransferase (nptII) resistance gene, hygromycin phosphotransferase (hpt), bromoxynil-specific nitrilase (bxn), phosphinotbricin acetyltransferase enzyme (BAR) and the spectinomycin resistance gene (spt), wherein the selective agent is kanamycin, hygromycin, geneticin, the herbicide glufosinate-ammonium ("Basta") or spectinomycin, respectively. Vectors may contain further sequences that allow for selection and propagation in a secondary host, such as an origin of replication and a selectable marker sequence. Typical secondary hosts include bacteria and yeast. In one embodiment, the secondary host is *Escherichia coli*, the origin of replication is a colE1-type, and the selectable marker is a gene encoding ampicillin resistance. Vectors of the invention may further comprise sequences that facilitate the integration of chimeric genes into plant chromosomes, such as regions of the Ti plasmid of *Agrobacterium tumifaciens*. Binary Ti-based vector systems that may be used to transfer polynucleotides are known to those of skill in the art, and many are commercially available (e.g., pBI121 Clontech Laboratories, Palo Alto, Calif.).

Depending on the vector, all or part of the expression vector's nucleic acid sequence may be transferred to the genome of the plant cell into which it is introduced. For instance, for binary vectors comprising left and right border regions from the Ti plasmid of *Agrobacterium*, the nucleic acid sequence inserted between left and right border sequences is generally transferred into a plant cell's genome, while the vector backbone sequence generally is not. Thus, when it is stated that a transgenic plant cell comprises a plant expression vector in its genome, it will be understood that it may only comprise the part of the vector that is normally transferred to the plant genome.

An important feature of the present invention is the bi-directionality of the isolated PRU promoter DNA. We have observed that the isolated promoter DNA is functional in either orientation; accordingly, the invention provides vectors in which the PRU promoter simultaneously controls seed-specific expression of two distinct heterologous genes, as well as methods for simultaneously controlling seed-specific expression of two heterologous genes. Such vectors typically comprise, in the 5' to 3' direction, a first heterologous gene in the antisense direction, a bi-directional PRU promoter, a second heterologous gene in the sense direction. Each heterologous gene may be associated with translational termination sequences in the appropriate position and orientation. A gene inhibition construct may replace one of the heterologous genes.

The invention provides the first example of a bi-directional promoter that controls similar seed-associated expression in each orientation. The bi-directionality of the isolated PRU promoter provides specific advantages for the genetic engineering of plants. First, the feature facilitates the introduction of multiple genes into plants, which is often necessary for metabolic engineering and trait stacking. Use of the bi-directional promoter may further avoid gene silencing, which may be induced by the repeated use of a single promoter in a cell.

The vectors described herein may form part of a plant transformation kit. Other components of the kit may include, but are not limited to, reagents useful for plant cell transformation.

Transgenic Plants and Plant Cells

Chimeric genes and constructs of the invention can be transferred to plant cells by any of a number of plant transformation methodologies. The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment, calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations.

In one embodiment, chimeric genes are introduced into plants by way of a T-DNA-less Ti plasmid carried by *Agrobacterium tumefaciens*, followed by co-cultivation of the *A. tumefaciens* cells with plant cells. In such cases, vectors for use in the invention contain a selectable marker gene to determine whether the transformation event was successful, T-DNA border regions from *Agrobactenum tumefaciens*, a heterologous gene of interest, and other elements as desired.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989, Plant Physiol 91:694–701), sunflower (Everett et al., 1987, Bio/Technology 5:1201), and soybean (Christou et al., 1989, Proc. Natl. Acad. Sci USA 86:7500–7504; Kline et al., 1987, Nature 327:70). Also of relevance are methods for transformation of prunin species, including almond (Miguel et al. 1999, Plant Cell Reports 18:387–93), cherry (Brasileiro et al. 1991, Plant Mol Biol 17:441–52; Dolgov et al. 1998, Acta Hort. [ISHS] 484:577–580), apricot and plum (Camara Machado et al. 1994, Euphytica 77:129–134; Ravelonandro et al. 1998, Acta Virol 42:270–2), and peach (Scorza et al. 1989, Acta Hort. (ISHS) 254:47–47).

The invention provides transgenic plants or progeny of these plants containing chimeric genes and constructs of the invention. Plant cells are transformed with the chimeric genes by any of the plant transformation methods. The transformed progenitor plant cell, usually in the form of a callus culture, leaf disk, explant or whole plant (e.g., via the vacuum infiltration method of Bechtold et al. 1993, CR Acad Sci 316:1194–1199) is regenerated into a complete transgenic plant by methods well known to one of ordinary skill in the art (e.g., Horsh et al., 1985). As used herein a "transformed progenitor cell" refers to a transformed cell that will directly or indirectly give rise to the transgenic plant. When the chimeric gene is carried in a vector containing a selectable marker gene is used, the progenitor cells may be cultured in medium containing the appropriate selection agent to identify and plant cells comprising the chimeric gene. Since progeny of transformed plants inherit the chimeric genes, seeds or cuttings from transformed plants may be used to maintain the transgenic line.

Presence of the chimeric gene or construct in transformed plants or plant cells may be detected using PCR, Southern blotting, or other known methods for detection of specific DNA sequences. Expression of the heterologous gene or inhibition of an endogenous gene may be assessed using Northern blotting, RT-PCR, or other known methods of detecting synthesis of specific mRNA species. If antibodies to the polypeptide encoded by the heterologous gene are available, Western analysis and immunohistochemical localization can be used to assess the production and localization of the polypeptide. Expression of a heterologous gene or inhibition of an endogenous gene may also be assessed by measuring the activity of the gene product, for instance using biochemical techniques described herein.

The methods described herein are generally applicable to all plants. Both monocotyledonous and dicotyledonous plants (monocots and dicots) are contemplated. In dicot crop plants, the embryo constitutes almost all of the seed, whereas in monocot crops, the embryo is a small part of the whole seed. The bulk of the monocot seed is comprised of endosperm, a triploid tissue that serves as an energy source for the germinating embryo. In monocots, it is expected that the PRU promoter will direct expression in the embryo and will therefore be useful for manipulation of embryos traits, such as oil content and oil quality, as well as the expression of embryonic storage proteins.

In a preferred application the invention is directed to fruit and nut plants of the *Prunus* genus, including almond, apricot, cherry, peach, and plum. In another preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling Brassica species, alfalfa (*Medicago sativa*), tobacco (*Nicotiana*), turfgrass (*Poaceae* family), other forage crops, and wild species that may be a source of unique fatty acids. The invention is further directed to model plant species, including *Arabidopsis thaliana*.

The chimeric genes, vectors, and transformed plants and plant cells described herein are useful for assaying derivatives of the isolated PRU promoter for seed-associated activity and for assessing the activity of a subject promoter in a specific plant species. For this use, the heterologous gene preferably encodes a protein whose expression is easily detected. For example, reporter genes, exemplified by chloramphenicol acetyl transferase and beta-glucuronidase (GUS; see, e.g., Jefferson et al. 1987, EMBO J. 6:3901–3907), are commonly used to assess transcriptional and translational competence of chimeric constructions. Other suitable genes include GFP (green florescence protein; Chalfie et al. (1994) Science 263:802), luciferase (Riggs et al. (1987) Nucleic Acids Res. 15(19):8115; Luehrsen et al. (1992) Methods Enzymol. 216:397–414) and genes encoding for anthocyanin production (Ludwig et al. (1990) Science 247:449). Standard assays are available to sensitively detect the reporter gene activity in a transgenic organism.

Seed-Associated Traits

The vectors, and chimeric genes and constructs of the present invention are useful for the genetic manipulation of plants and for the production of plants having desired traits, particularly seed-associated traits. Transgenic plants, transgenic plant cells and transgenic seed of the invention may also be a useful source of recombinantly expressed material.

Various seed-associated traits are of interest. In one embodiment of the invention, a PRU promoter is used to modify the quantity and/or composition of carbohydrates, lipids (especially fatty acids), and/or amino acids in seed. Accordingly, heterologous genes of interest include those involved in oil, starch, carbohydrate and nutrient metabolism, as well as those alThcting kernel size, sucrose loading, and the like. In one specific application of the invention, the brazil nut 2S albumin gene (Muntz et al., Nahrung 1998 Aug;42(3–4):125–7) is expressed in seed to alter amino acid composition. In other applications, lipid metabolism genes are expressed to alter the content and/or composition of seed oils. Exemplary lipid metabolism genes include desaturases (see, e.g., U.S. Pat. Nos. 5,552,306 and 5,614,393), acyl carrier proteins (ACPs), thioesterases, acetyl transacylases, acetyl-coA carboxylases, ketoacyl-synthases, malonyl transacylases, and elongases. Such lipid metabolism genes have been isolated and characterized from a number of different bacteria and plant species. Specific genes whose altered expression in seed has been shown to cause modified lipid phenotypes include diacylglycerol acyltransferase (Jako et at, 2001, Plant Physiol 2001, 126:861–74), modified ACP desaturase (Cahoon and Shanldin, 2000, Proc Natl Acad Sci USA 97:12350–5), phytoene synthase (Shewmaker et al., 1999, Plant J 20:401–412), acetyl-coenzyxne A carboxylase (Roesler et al., 1997, Plant Physiol 113:75–81), beta-Ketoacyl-CoA synthase (Lassner et at, 1996, Plant Cell 1996, 8:281–92), sn-2 acyltransferase (Zou et at, 1997, Plant Cell 9:909–23), acyl-ACP thioesterases and gycerolipid hydroxylase.

Additional genes of interest encode important traits for agronomics, such as insect resistance, disease resistance, herbicide resistance, and grain characteristics. The invention also permits the seed-associated expression of pharmaceutically or industrially important proteins.

An important aspect of the invention is the ability to limit the expression of a heterologous gene under control of a PRU promoter to the seed of a transgenic plant. Altering the primary metabolic pathways that control carbohydrate, lipid, and/or amino acid production may have detrimental consequences on plant performance or yield if these metabolic changes occur in all tissues of the plant. For example, the global elimination of polyunsaturated fatty acid production results in plants that are no longer photoautotrophic (McConn and Browse 1998, Plant J. 15:521–30); however, when such fatty acid alterations are confined to seed, they have had no affect on plant productivity (Mazur et al. 1999, Science 285:372–5). For other applications, a desired trait may depend on the localized toxicity of the gene product. For instance, expression of genes that are deleterious or toxic may be used to create seedless plant varieties.

All publications cited herein, including patents, patent applications, and sequence information in referenced websites, are expressly incorporated by reference for the purpose of describing and disclosing compositions and methodologies that might be used in connection with the invention.

EXAMPLES

Example 1

Isolation of a Cherry Globulin Promoter Fragment

The genus Prunus is represented by a number of commercially important fruits and nuts, including almond, apricot, cherry, peach and plum. Based on taxonomic proximity, it was hypothesized that genes encoding the major seed storage proteins would show sequence conservation in Prunus species. Conserved regions of the almond Pru1 and Pru2 sequences were used to amplify the major seed storage protein genes from cherry genomic DNA.

A PCR-accessible genomic library was constructed from DNA extracted from cherry leaves (*Prunus avium*). Oligonucleotide primers were designed complementary to the 5' sequence of the Pru1 prunin cDNA clone (GenBank accession ×78119, gil460805) from almond (pru1 PFa, SEQ ID NO:4; pru1 PFb, SEQ ID NO:5) and were used to amplify a genomic fragment of upstream sequence from a set of cherry (*Prunus avium*) promoter finder (PF) libraries. The amplification resulted in a 1.2 kb fragment present in all of the promoter finder libraries, which was an interesting result since the products from each separate library are determined by the position of a unique restriction site.

The 1.2 kb amplification product from the DraI library was cloned into the pCR2.1 cloning vector and sequenced.

Nucleotide sequence analysis confirmed that a region of the 1.2 kb fragment is indeed homologous, but not identical, to Pru1 from almond. A BLASTN search revealed that the 100 bases at the 3' end of the fragment shared significant homology to *P. amygdalus* pru1 mRNA (HS=201, P(N)= 3.3e-13), and to no other sequences in GenBank.

Furthermore, the primer sequence complementary to Pru1 was detected on both the 5' and 3' ends of the clone, which would explain the unusual result of the genomic DNA amplification. The results indicated that there are two homologous Prunin-like genes in the cherry genome that are in opposite orientations and separated by 1.2 kb of upstream sequence. A single EcoRI site occurs in the center of the sequence. It can also be inferred, due to the absence of any other amplification products from the PF libraries, these may be the only two copies of Prunin-like genes in the cherry genome.

The complete sequence of the 1.2 kb fragment was determined and is presented as SEQ ID NO:1. The gene in the orientation with the highest homology (i.e., of coding sequences) to almond Pru1 has been called chPru1, and the gene in the opposite orientation was designated as chPru2. The sequence of SEQ ID NO:1 was flanked with NcoI restriction enzyme sites (CCATGG), which were engineered around the predicted translational start sites of ChPru1 and ChPru2. In the forward orientation, a TATA-box and a motif with homology to a legumin box, which has been shown to direct seed-specific expression of globulins, were identified at nucleotides 1169–1175 and nucleotides 1092–1098, respectively. In the reverse orientation, a TATA-box and the legumin-box-like motif were identified at the reverse complements of nucleotides 95–100 and nucleotides 170–176, respectively, of SEQ ID NO:1. Alignment of the chPru1 and chPru2 upstream sequences (i.e., SEQ ID NO:1 and the reverse complement thereof, SEQ ID NO:6), as depicted in FIG. 1, shows regions of conservation between the two promoters around the putative TATA-box, the legumin-box-like motif, and a conserved motif at approximately −350 from the translational start (nucleotides 885–911 in the forward orientation and the reverse complement of nucleotides 372–438 in the reverse orientation).

Nucleotide sequence homology searching using the complete chPru upstream sequence (blastn against all.na) revealed some similarity between the putative chPru2 5' UTR and the 5' flanking regions of the legumin genes from pea, as shown in Table 1. The region of similarity begins at position 1028 in the PRU promoter of the forward orientation (i.e., as presented in SEQ ID NO:1), which is in the vicinity of the legumin-box-like motif, and extends through position 1235, which is in the predicted 5'UTR of the chPru2 gene.

TABLE 1

| Sequences producing High-scoring Segment Pairs | | BLAST scores | | |
|---|---|---|---|---|
| Accession Number | Sequence Definition | Score | Probability P(N) | Published References |
| gi\|15384822\|emb\|AL590439.12 | Human DNA sequence from clone RP11-394I23 on chromosome 10 | 367 | 5.0e−06 | |
| gi\|20626\|emb\|X57666.1 | *P. sativum* DNA for 5`flanking region of legumin gene LegA2 | 298 | 1.6e−05 | Rerie et al., 1991, Mol Gen Genet 225: 148–57 |
| gi\|20780\|emb\|X02983.1 | Pea legB gene (legumin) 5' flanking region | 298 | 0.0049 | Lycett et al., 1985, Nucleic Acids Res 13: 6733–43 |
| gi\|20781\|emb\|X02984.1 | Pea legC gene (legumin) 5' flanking region | 298 | 0.0054 | Lycett et al., 1985. |
| gi\|7339556\|emb\|AJ276878.1 | *Pisum sativum* partial legA gene for legumin, promoter region and exon 1 | 298 | 0.0064 | |
| gi\|20777\|emb\|X02982.1 | Pea legA gene for legumin | 298 | 0.0066 | Lycett et al., 1985. |

Example 2

Identification of Seed Storage Proteins in Apricot, Peach, Plum, Melon and Tomato A survey of seed storage proteins was initiated to identify other fruit and vegetable species that have 12S globulin as a major seed storage protein. Embryos were isolated from seeds of apricot, peach, plum, melon and tomato. Albumins and globulins were separated on the basis of differential solubility, separated by SDS-PAGE, and stained with Coomassie blue. The presence of 12S globulins was confirmed in apricot, peach, and plum seeds (embryos). Major polypeptide doublets at approximately 20 kDa and 36–38 kDa were present in the proteins extracted from these embryos. These results confirmed the presence of globulins as a major seed storage protein in the Prunus genera. In contrast, the major seed storage proteins of tomato and melon were present as abundant polypeptides of approximately 32 and 45 kDa. The polypeptides of melon and tomato are salt-soluble, which suggests they are globulins but of a different molecular mass than the prunins. These experiments suggest that the PRU promoter will be active in plants of the Prunus genus.

Example 3

Characterization of the chPRU Promoters in *Arabidopsis*

We assessed the strength and specificity of the isolated chPRU promoters in *Arabidopsis*, a dicot oilseed plant. The assay system used chimeric genes comprising the FAD2 cDNA, encoding a fatty acid desaturase, under control of chPRU promoters. A loss-of-function mutation in endogenous FAD2 ("fad2-1") affects fatty acid composition in both seeds and leaves of affected plants (Okuley et al. 1994, Plant Cell 6:147–158). We tested the ability of the chimeric genes to complement the lipid defects in transgenic fad2-1 plants. We compared leaf- and seed-oil composition in fad2-1 mutant plants to that of mutant plants transformed with FAD2 cDNA under the control of a PRU promoter or a strong constitutive promoter Constructs. Reporter constructs were created to test the activity and tissue specificity of the candidate bidirectional ChPru promoter in each orientation. The ChPru promoter was inserted in both orientations into a binary vector construct such that it was driving expression of the FAD2 gene in one orientation and the uid gene encoding GUS in the other orientation. The GUS coding sequence was under control of a Nos 3' termination sequence from *Agrobacterium* ("NosT;" Depicker et al., 1983, J Mol Appl Genet 1: 561–573).

The FAD2 coding region and 3'UTR were PCR-amplified from a cDNA clone using a high fidelity polymerase, and an NcoI site was engineered around the ATG start codon. The FAD2 coding region was then fully sequenced and subcloned upstream of a GUS gene. The chPRU promoter was PCR-amplified from the Cherry Genome Walker Primary PCR reaction, and NcoI sites added around the start codons at either end. This promoter fragment was cloned into an intermediate vector and fully sequenced, then subcloned in both orientations into the unique NcoI site between the FAD2 and GUS coding regions. The FAD2/chPRU/Gus/NosT cassettes comprising chPRU in both orientations were isolated and cloned into a modified plant expression vector. A kanamycin resistance plant selection cassette, comprising the nptII gene (Beck et al., 1982, Gene 19:327–36) under control of the strong constitutive CsVMV promoter (Verdaguer et al., 1996, Plant Mol Biol 31:1129–39) and the *Agrobacterium* gene 7 ("G7") termination sequence, was cloned into both constructs at a unique restriction site adjacent to the T-DNA right border (RB) (Velten and Schell, 1985, Nucleic Acids Res 13:6981–98). pAG4021 contains the FAD2 coding sequence under the transcriptional control of the chPRU promoter in the chPru1 orientation (reverse complement of the sequence presented in SEQ ID NO:1), while pAG4022 contains FAD2 under the control of the promoter in the chPru2 orientation.

In addition, a constitutive FAD2 expression construct was generated as a positive control. pAG4708 contains the FAD2 coding region under the control of the CsVMV promoter and NosT. PAG4708 also contains a selection cassette composed of the nptII gene under control of the RE4 constitutive promoter (U.S. Pat. No. 6,054,635) and the G7 termination sequence, cloned in a site adjacent to the T-DNA left border (LB). The plant expression constructs utilized the pPZP200 binary vector (Hajdukiewicz et al., 1994, Plant Mol Biol 25: 989–94).

The plant expression constructs were first transformed into the *Agrobacterium* strain GV3101 (pMP90RK helper plasmid) and subsequently introduced into *Arabidopsis thaliana*, fad2-1 mutant, by a modified in planta protocol (from Bechtold et al., 1993, supra). Transformants were selected on 0.5×MS supplemented with 100 μg/ml kanamycin.

Fatty acid methyl ester (FAME) analysis. Fatty acid methyl esters were prepared from leaves and seeds of transformant lines carrying the three above-described constructs and control lines (both wild type Col-0 and fad2 mutant). Quantitative determination of leaf and seed fatty acid composition was performed as follows. Either whole seeds or cut leaves were trans-esterified in 500 μl 2.5% $H_2SO_4$ in MeOH for 3 hours at 80 degrees C., following the method of Browse et al. (Biochem J 235:25–31, 1986) with modifications. A known amount of heptadecanoic acid was included in the reaction as an internal standard. 750 μl of water and 400 μl of hexane were added to each vial, which was then shaken vigorously and allowed to phase separate. Reaction vials were loaded directly onto GC for analysis, and the upper hexane phase was sampled by the autosampler. Gas chromatography with Flame Ionization detection was used to separate and quantify the fatty acid methyl esters. Agilent™ 6890 Plus GCs were used for separation with Agilent Innowax™ columns (30 m×0.25 mm ID, 250 μm film thickness). The carrier gas was hydrogen at a constant flow of 2.5 ml/minute. 1 μl of sample was injected in splitless mode (inlet temperature 220° C., Purge flow 15 ml/min at 1 minute). The oven was programmed for an initial temperature of 105° C., Initial Time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis was using the Millennium™ Chromatography Management System (Version 3.2, Waters Corporation, Milford, Mass.). Integration and quantification was performed automatically by the Millennium™ software.

Statistical Analysis. Descriptive statistics were calculated using Microsoft Excel 97(Microsoft Inc) SR-2 and the included Analysis Tool Pak.

Results. The FAD2 gene product produces 18:2 (linoleate) fatty acids from 18:1 in both leaves and seeds. Linoleate can be further converted to 18:3 (Linolenate) by other desaturase enzymes in leaves. Thus, in leaves, comparing 18:1 and the sum of 18 carbon polyunsaturates (i.e., 18:2+18:3) provided a good indication of thefad2 mutation and the degree of complementation by the introduced wild type cDNA. Results of FAME analysis of leaves are summarized in Table 2. For each transformant or control line tested, single leaves from each of 24 Ti plants were analyzed. The average contents of 18:1 and 18:2+18:3 fatty acids as a percentage of total fatty acids are shown with standard deviation in parentheses.

TABLE 2

Leaf Fatty Acid Composition.

| LINE | 18:1 | 18:2 + 18:3 |
|---|---|---|
| Col-0 | 2.79 (0.96) | 62.90 (1.51) |
| fad2-1 | 18.10 (1.73) | 43.58 (2.12) |
| fad2-1, pAG4708 | 8.16 (4.27) | 54.28 (3.51) |
| fad2-1, pAG4021 | 17.12 (1.69) | 45.08 (1.64) |
| fad2-1, pAG4022 | 14.41 (2.22) | 46.88 (1.38) |

The control fad2-1 mutant displayed the expected high level of 18:1 fatty acids (~18% of total fatty acids, compared to only ~3% of the total in wild type). The average 18:1 content of CsVMV-FAD2 (pAG4708) transformants was 8%, which represented a range of complementation from nearly complete, to not observable. Five of 22 transformants had an 18:1 content of 3% or less total fatty acids—the maximum amount of 18:1 observed in any of the wild type individuals—indicating that 22% of the transformants displayed full complementation of the fad2-1 mutation. We anticipated that the degree of transgene expression in independent transformants would vary greatly for a variety of reasons, and thus these results were consistent with our expectations. The 18:1 content in leaves of transformants carrying FAD2 under control of the chPRU promoter in both orientations was somewhat reduced compared to fad2-1 mutant, reflecting the small number of the transformants that had a modest degree of complementation in leaves. Full complementation was never observed in leaves comprising the chPRU promoter in either orientation. The PRU promoter in either orientation is clearly far less effective than the CsVMV promoter at complementing the phenotype in leaves.

The results of seed fatty acid analysis are summarized in Table 3. T2 seeds were harvested from the same T1 individuals analyzed for leaf fatty composition (Table 2). The average contents of 16:0, 18:0, 18:1, 18:2, 18:3, 20:0, and 20:1 fatty acids as a percentage of total fatty acids are shown. Total content of mono-unsaturates (18:1+20:1) is also shown. Standard error was less than 5% of the reported value in all cases.

TABLE 3

Seed Fatty Acid Composition.

| Line | 16:0 | 18:0 | 18:1 | 18:2 | 18:3 | 20:0 | 20:1 | Mono-unsaturates |
|---|---|---|---|---|---|---|---|---|
| Col-0 | 8.86 | 3.84 | 14.25 | 30.43 | 21.72 | 2.44 | 18.45 | 32.70 |
| fad2-1 | 5.84 | 3.40 | 55.57 | 3.03 | 7.74 | 1.66 | 22.76 | 78.33 |
| fad2-1, Pag4021 | 6.94 | 3.88 | 33.44 | 17.06 | 15.51 | 2.28 | 20.90 | 54.33 |
| fad2-1, pAG4022 | 7.40 | 3.65 | 32.81 | 17.57 | 15.71 | 1.97 | 20.90 | 53.71 |
| fad2-1, pAG4708 | 7.28 | 3.81 | 39.65 | 11.11 | 13.06 | 2.31 | 22.77 | 62.42 |

The large amount of 18:1 and 20:1 fatty acids in fad2-1 mutant as compared to the wild type Col-0 is a result of the loss of function mutation. It is immediately evident from the data that the CsVMV promoter performed far less effectively in seeds. The total monounsaturate content of 62.42% in pAG4708 transformants is closest to the fad2-1 mutant value of 78.3%. Expression driven by chPRU in both orientations produced greater reductions in total monounsaturates than the CsVMV promoter.

When individual plant lines were analyzed, the chPRU transformants represented a range of complementation from intermediate to complete complementation. More importantly, when the frequency of "full-complementation," or complete restoration of the wild-type composition in the transformed mutant plant, is considered, PRU dramatically outperformed the CsVMV promoter. Table 4 shows the percentage of transformants displaying full-complementation of the fad2-1 phenotype in leaves and seeds when CsVMV and chPRU promoters drive FAD2 expression.

TABLE 4

Transformants displaying full complementation of the fad2 phenotype in leaves and seed.

| Line | Leaf | Seed |
|---|---|---|
| fad2-1, pAG4021 | 0% | 18% |
| fad2-1, pAG4022 | 0% | 20% |
| fad2-1, pAG4708 | 23% | 0% |

The differential effectiveness of chPRU-driven expression in seeds (high complementation) versus leaves (absence of complementation), and the promoters' successful complementation of the seed phenotype of fad2-1 mutants (especially as compared to the CsVMV promoter) directly support the utility of PRU promoters in controlling seed-directed gene expression in a variety of dicot plants, including oilseeds.

GUS Assays: Using the same Pru transgenic lines assayed biochemically, reporter gene assays were performed on staged siliques in order to 1) confirm the developmental activity of the chPru promoter, and 2) confirm that the promoter directs heterologous gene expression simultaneously in both orientations.

Staging Arabidopsis Siliques: Three Pru2-1 events & three Pru1-2 events that showed a high degree of fad2-1 complementation were selected for GUS enzyme assays. T2 seed were selected on kanamycin and 36 seedlings per event were transplanted to soil.

Upon flowering, individual siliques were tagged with loops of colored thread. Tagging proceeded for a total of fourteen days, with a different color tag used for each successive two-day bin (0–1 DAF through 12–13 DAF).

Siliques were harvested at the end of the fourteen-day tagging period. They were pooled according to event and bin. Siliques were homogenized to extract protein, and the extracts were mixed with an assay buffer containing the fluorogenic substrate 4-methylumbelliferyl β-D-glucuronide (MUG). Fluorescence intensity was measured at one hour intervals over the course of three hours. GUS activity was normalized to total protein concentration to determine standard GUS reporter activity.

Results: GUS activity was measured during silique development. Three different events each of chPru1::GUS and chPru2::GUS were compared to four events of CsVMV::GUS and to Col-0. The following was observed:

Events that showed a high level of FAD2 expression also showed relatively high levels of GUS expression when compared to the activity of the CsVMV promoter.

GUS activity assays confirmed that the CsVMV promoter is active throughout silique development at a relative constant level in any single event.

The chPru promoter is relatively inactive during the early stages of silique development (0 to 3 DAF).

chPru promoter activity peaks around 10 to 11 DAF.

Peak chPru promoter activity is equal to the peak activity of the CsVMV promoter.

The chPru1 promoter appears to become active slightly earlier than the Pru2 promoter (6 DAF vs 8 DAF).

We claim:

1. An isolated nucleic acid molecule comprising a PRU promoter that has seed-associated promoter activity and that comprises, in a 5' to 3' direction:
   (a) nucleotides 1055–1127 of SEQ ID NO:1 or the reverse complement of nucleotides 142–214 of SEQ ID NO:1, operably linked to
   (b) nucleotides 1168–1212 of SEQ ID NO:1 or the reverse complement of nucleotides 58–101 of SEQ ID NO:1.

2. The isolated nucleic acid molecule of claim 1 wherein the PRU promoter additionally comprises nucleotides 854–918 of SEQ ID NO:1 or the reverse complement of nucleotides 365–428 of SEQ ID NO:1 operably linked to the nucleotides set forth in (a) and (b).

3. The isolated nucleic acid molecule of claim 1 wherein the PRU promoter comprises nucleotides 1055–1212 of SEQ ID NO:1.

4. The isolated nucleic acid molecule of claim 3 wherein the PRU promoter comprises nucleotides 854–1212 of SEQ ID NO:1.

5. The isolated nucleic acid molecule of claim 4 wherein the PRU promoter comprises SEQ ID NO:1.

6. The isolated nucleic acid molecule of claim 1 wherein the PRU promoter comprises the reverse complement of nucleotides 58–214 of SEQ ID NO:1.

7. The isolated nucleic acid molecule of claim 6 wherein the PRU promoter comprises the reverse complement of nucleotides 58–428 of SEQ ID NO:1.

8. The isolated nucleic acid molecule of claim 7 wherein the PRU promoter comprises the reverse complement of SEQ ID NO:1.

9. The isolated nucleic acid molecule of claim 1, wherein the nucleic acid molecule is a plant expression vector.

10. The plant expression vector of claim 9, wherein the PRU promoter is operably linked to a heterologous protein-encoding sequence.

11. The plant expression vector of claim 9 comprising a first heterologous protein-encoding sequence in the antisense direction, the PRU promoter, and a second heterologous protein-encoding sequence in the sense direction, wherein the vector is double-stranded, and wherein the PRU promoter directs seed-associated expression of both the first and the second heterologous protein-encoding sequences.

12. A transgenic plant cell comprising a plant expression vector of claim 9 in its genome.

13. The plant cell of claim 12, wherein the plant cell is from a plant belonging to the *Prunus* genus.

14. The plant cell of claim 13, wherein the plant is selected from the group consisting of cherry, almond, peach, apricot, and plum.

15. The plant cell of claim 12, wherein the plant is from the *Arabidopsis* genus.

16. A method for producing a transgenic plant that exhibits seed-associated expression of a heterologous protein-encoding sequence, comprising:
   transforming progenitor cells of the plant with the plant expression vector of claim 10, and
   growing the transformed progenitor cells to produce a transgenic plant that exhibits seed-associated expression of the heterologous protein-encoding sequence.

17. A transgenic plant comprising the cell of claim 12.

18. The plant of claim 17, wherein the plant belongs to the *Prunus* genus.

19. The plant of claim 18, wherein the plant is selected from the group consisting of cherry, almond, peach, apricot, and plum.

20. The plant of claim 17, wherein the plant belongs to the *Arabidopsis* genus.

21. A plant part obtained from a plant according to claim 17.

22. The plant part of claim 21, wherein the plant part is a seed.

23. The nucleic acid of claim 1, wherein the PRU promoter comprises, in a 5' to 3' direction, nucleotides 1055–1127 of SEQ ID NO:1 operably linked to nucleotides 1168–1212 of SEQ ID NO:1.

24. The nucleic acid of claim 23, wherein the PRU promoter further comprises nucleotides 854–918 of SEQ ID NO:1.

25. The nucleic acid of claim 1, wherein the PRU promoter comprises, in a 5' to 3' direction, the reverse complement of nucleotides 142–214 of SEQ ID NO:1 operably linked to the reverse complement of nucleotides 58–101 of SEQ ID NO:1.

26. The nucleic acid of claim 1, wherein the PRU promoter further comprises the reverse complement of nucleotides 365–428 of SEQ ID NO:1.

* * * * *

UNITED STATES PATENT AND TRADEMARK OFFICE
CERTIFICATE OF CORRECTION

PATENT NO.       : 7,179,960 B2                                             Page 1 of 1
APPLICATION NO.  : 10/633279
DATED            : February 20, 2007
INVENTOR(S)      : Clendennen et al.

It is certified that error appears in the above-identified patent and that said Letters Patent is hereby corrected as shown below:

Column 2, line 63, "wbich" should be --which--.
Column 4, line 66, "seed-specifidty" should be --seed-specificity--.
Column 5, line 13, "wit an" should be --with an--.
Column 6, line 42, "0.1Ficol™" should be --0.1% Ficoll™--.
Column 7, line 27, "promoten Thus," should be --promoter. Thus,--.
Column 8, line 34, "chimetic" should be --chimeric--.
Column 8, line 43, "phosphinotbricin" should be --phosphinothricin--.
Column 9, line 65, "*Agrobactenum*" should be --*Agrobacterium*--.
Column 11, line 55, "alThcting" should be --affecting--.
Column 12, line 4, "Shanldin" should be --Shanklin--.
Column 12, line 6, "acetyl-coenzyxne" should be --acetyl-coenzyme--.
Column 12, line 8 "(Lassner et at," should be --(Lassner et al.,--.
Column 12, line 9 "(Zou et at," should be --(Zou et al.,--.
Column 12, line 10 "gycerolipid" should be --glycerolipid--.
Column 12, line 58 "x78119" should be --X78119--.
Column 13, line 47 "chPrul1" should be --chPru1--.
Column 16, line 39 "thefad2" should be --the*fad2*--.
Column 16, line 43 "Ti" should be --T1--.

Signed and Sealed this

Twenty-eighth Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,179,960 B2  Page 1 of 1
APPLICATION NO. : 10/633279
DATED : February 20, 2007
INVENTOR(S) : Clendennen et al.

It is certified that error appears in the above-identified patent and that said Letters Patent is hereby corrected as shown below:

Column 2, line 63, "wbich" should be --which--.
Column 4, line 66, "seed-specifidty" should be --seed-specificity--.
Column 5, line 13, "wit an" should be --with an--.
Column 6, line 42, "0.1Ficol™" should be --0.1% Ficoll™--.
Column 7, line 27, "promoten Thus," should be --promoter. Thus,--.
Column 8, line 34, "chimetic" should be --chimeric--.
Column 8, line 43, "phosphinotbricin" should be --phosphinothricin--.
Column 9, line 65, *"Agrobactenum"* should be --*Agrobacterium*--.
Column 11, line 55, "alThcting" should be --affecting--.
Column 12, line 4, "Shanldin" should be --Shanklin--.
Column 12, line 6, "acetyl-coenzyxne" should be --acetyl-coenzyme--.
Column 12, line 8 "(Lassner et at," should be --(Lassner et al.,--.
Column 12, line 9 "(Zou et at," should be --(Zou et al.,--.
Column 12, line 10 "gycerolipid" should be --glycerolipid--.
Column 12, line 58 "x78119" should be --X78119--.
Column 13, line 47 "chPru11" should be --chPru1--.
Column 16, line 39 "thefad2" should be --the *fad2*--.
Column 16, line 43 "Ti" should be --T1--.

This certificate supersedes the Certificate of Correction issued August 28, 2007.

Signed and Sealed this

First Day of July, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 1255
<212> TYPE: DNA
<213> ORGANISM: Prunus avium

<400> SEQUENCE: 1

```
cacaaggaat gagaaggaga tagatgactt gtgattcgag ctcacttgta tcttgtgttt        60
gagatggtga agcaacgagc ggtgggcgct ggtatttgta ggagggaaaa tgagttgagg       120
cgtggacacg tagagtttcg tgtgtaaggc atcttttgcc attcttctac ttgcatggct       180
ttgaggcttt gaattgttaa cacctcattt tgtgtagcag gggcagcagg ctatatgcgg       240
caaccagcgg tggggttcct cgtcaatatt gttgtctggt tctgagcttg atttgcacct       300
ggccgtttgg tgaagtaaaa ttcatgggac ttgggatccg aacccgggcc catatgactg       360
tgcgtgcttg gtgagaaacg tgaactccac ctgattgtct gtgatgagtt taattggttt       420
tttttgttta aatgtttggt caaatttgtt ttactcggaa caaattgtta agcctctgct       480
ctataagaaa taaaaaacgt tgttttgtga actaaaacgc aatcttttgg cttagttgag       540
ccaagagggt tctctctcta cagttccaaa tccaaaaccc acaacttcaa tgaaattacg       600
aatgaatgac ctccactacc actagtatga attcttttgt attttcctgt caagcaaaaa       660
ggccaacaag agatcagcta cttagaacaa caaaagcatt tcatacttta caaattgatc       720
ctataaaaaa cttggaagct tttctttaaa agaaaaaaag gagagagaat attagagtgg       780
tacccaaatt ataataactc aaatatttac ttttacataa aaggagagag aatatgaatg       840
aggattggca acaaaacaat ggaacccacc aaaactgatc agagacgatc agatggagtt       900
cacgtttctc agcaggcaat gccaaaaggg tttcagaaac gcaccaatcc caagacagta       960
agaaaacaac aatggctcga gacacccacc tggttgccac ataactcaac tcactttgtt      1020
ttttctctga agccgaaagc cacctgccct aaaccacaaa atgaggtgta acaattcag       1080 agcttcaaag ccatgcaagc agaataatgg cgaaggattc cttacactca tttccctacg      1140
tgtctctccc tcacctcctc ttcttcacta taaataccag cgcctgctgc tcgccgcttc      1200
acccatctca aaaccaaaga gctttctctc tcctttctgt agtctccaaa tatgt           1255
```

<210> SEQ ID NO 2
<211> LENGTH: 239
<212> TYPE: DNA
<213> ORGANISM: Prunus avium
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (227)..(229)
<223> OTHER INFORMATION: n is a, c, g, or t
<220> FEATURE:
<221> NAME/KEY: misc_feature
<222> LOCATION: (232)..(235)
<223> OTHER INFORMATION: n is a, c, g, or t

```
<220> FEATURE:
<221> NAME/KEY: misc_feature
<222> LOCATION: (238)..(238)
<223> OTHER INFORMATION: n is a, c, g, or t

<400> SEQUENCE: 2
atggctaagg ctttcgtttt ttcgctttgc ttgcttctgg ttttcaatgg ctgcttagcg      60
gcacgtcagt cccagttgag tccgcagaac cagtgccagc tcaaccagct tcaagcccgc     120
gaacaagccg aattctgcag atatccatca cactggcggc cgctcgagca tgcatctaga    180
gggcccaatt cgccatatgg accatggcca nacaggacag nttnccnnna cnnnnccnc     239

<210> SEQ ID NO 3
<211> LENGTH: 162
<212> TYPE: DNA
<213> ORGANISM: Prunus avium
<220> FEATURE:
<221> NAME/KEY: misc_feature
<222> LOCATION: (154)..(155)
<223> OTHER INFORMATION: n is a, c, g, or t
<220> FEATURE:
<221> NAME/KEY: misc_feature
<222> LOCATION: (157)..(161)
<223> OTHER INFORMATION: n is a, c, g, or t

<400> SEQUENCE: 3
atgtctatgc ctttagctct cgcttctctt tgcttgcttc ttcttttcaa tggctgcctg      60
gcttcccgcc agcatatatt tggccagaac aaagagtggc agctcaacca gcttcaagcc    120
cgcgaacaag ccgaattcca gcacactggc ggcnncnnnn nc                        162

<210> SEQ ID NO 4
<211> LENGTH: 28
<212> TYPE: DNA
<213> ORGANISM: Prunus avium

<400> SEQUENCE: 4
gttcgcgggc ttgaagctgg ttgagctg                                         28

<210> SEQ ID NO 5
<211> LENGTH: 28
<212> TYPE: DNA
<213> ORGANISM: Prunus avium

<400> SEQUENCE: 5
gcagccattg aaaaccagaa gcaagcaa                                         28

<210> SEQ ID NO 6
<211> LENGTH: 1255
<212> TYPE: DNA
<213> ORGANISM: Prunus avium

<400> SEQUENCE: 6
acatatttgg agactacaga aaggagagag aaagctcttt ggttttgaga tgggtgaagc      60
ggcgagcagc aggcgctggt atttatagtg aagaagagga ggtgagggag agacacgtag    120
ggaaatgagt gtaaggaatc cttcgccatt attctgcttg catggctttg aagctctgaa    180
ttgtttacac ctcatttttgt ggtttagggc aggtggcttt cggcttcaga gaaaaaacaa    240
agtgagttga gttatgtggc aaccaggtgg gtgtctcgag ccattgttgt tttcttactg    300
tcttgggatt ggtgcgtttc tgaaacccctt ttggcattgc ctgctgagaa acgtgaactc    360
catctgatcg tctctgatca gttttggtgg gttccattgt tttgttgcca atcctcattc    420
```

```
atattctctc tccttttatg taaaagtaaa tatttgagtt attataattt gggtaccact    480
ctaatattct ctctcctttt tttcttttaa agaaaagctt ccaagttttt tataggatca    540
atttgtaaag tatgaaatgc ttttgttgtt ctaagtagct gatctcttgt tggccttttt    600
gcttgacagg aaaatacaaa agaattcata ctagtggtag tggaggtcat tcattcgtaa    660
tttcattgaa gttgtgggtt ttggatttgg aactgtagag agagaaccct cttggctcaa    720
ctaagccaaa agattgcgtt ttagttcaca aaacaacgtt tttatttct tatagagcag    780 aggcttaaca atttgttccg agtaaaacaa atttgaccaa acatttaaac aaaaaaaacc    840
aattaaactc atcacagaca atcaggtgga gttcacgttt ctcaccaagc acgcacagtc    900
atatgggccc gggttcggat cccaagtccc atgaatttta cttcaccaaa cggccaggtg    960
caaatcaagc tcagaaccag acaacaatat tgacgaggaa ccccaccgct ggttgccgca   1020
tatagcctgc tgcccctgct acacaaaatg aggtgttaac aattcaaagc ctcaaagcca   1080
tgcaagtaga agaatggcaa aagatgcctt acacacgaaa ctctacgtgt ccacgcctca   1140
actcattttc cctcctacaa ataccagcgc ccaccgctcg ttgcttcacc atctcaaaca   1200
caagatacaa gtgagctcga atcacaagtc atctatctcc ttctcattcc ttgtg        1255
```

<210> SEQ ID NO 7
<211> LENGTH: 44
<212> TYPE: DNA
<213> ORGANISM: Prunus avium

<400> SEQUENCE: 7

```
tataaatacc agcgcctgct gctcgccgct tcacccatct caaa               44
```

<210> SEQ ID NO 8
<211> LENGTH: 73
<212> TYPE: DNA
<213> ORGANISM: Prunus avium

<400> SEQUENCE: 8

```
cacaaaatga ggtgtaaaca attcagagct tcaaagccat gcaagcagaa taatggcgaa    60
ggattcctta cac                                                      73
```

<210> SEQ ID NO 9
<211> LENGTH: 65
<212> TYPE: DNA
<213> ORGANISM: Prunus avium

<400> SEQUENCE: 9

```
aaacaatgga acccaccaaa actgatcaga gacgatcaga tggagttcac gtttctcagc    60
aggca                                                               65
```

<210> SEQ ID NO 10
<211> LENGTH: 43
<212> TYPE: DNA
<213> ORGANISM: Prunus avium

<400> SEQUENCE: 10

```
tacaaatacc agcgcccacc gctcgttgct tcaccatctc aaa                43
```

<210> SEQ ID NO 11
<211> LENGTH: 74
<212> TYPE: DNA
<213> ORGANISM: Prunus avium

<400> SEQUENCE: 11

```
acaaaatgag gtgttaacaa ttcaaagcct caaagccatg caagtagaag aatggcaaaa        60
gatgccttac acac                                                         74

<210> SEQ ID NO 12
<211> LENGTH: 65
<212> TYPE: DNA
<213> ORGANISM: Prunus avium

<400> SEQUENCE: 12
aaacaaaaaa aaccaattaa actcatcaca gacaatcagg tggagttcac gtttctcacc        60
aagca                                                                   65
```